United States Patent [19]
Nath

[11] Patent Number: 5,165,773
[45] Date of Patent: Nov. 24, 1992

[54] FLEXIBLE LIGHT GUIDE HAVING A LIQUID CORE AND ILLUMINATING DEVICE INCLUDING A LIGHT GUIDE OF THIS TYPE

[76] Inventor: Genther Nath, Delpstrasse 27, D-8000 Muenchen 80, Fed. Rep. of Germany

[21] Appl. No.: 738,959

[22] Filed: Jul. 31, 1991

[30] Foreign Application Priority Data

Aug. 1, 1990 [DE] Fed. Rep. of Germany ....... 4024445

[51] Int. Cl.$^5$ ............................................. F21V 8/00
[52] U.S. Cl. .................................... 362/32; 362/318; 385/125
[58] Field of Search ............................ 362/32, 318, 56; 356/96.32; 385/125, 126

[56] References Cited

U.S. PATENT DOCUMENTS

| | | |
|---|---|---|
| 3,740,113 | 6/1973 | Cass . |
| 3,920,980 | 11/1975 | Nath ...................... 362/32 |
| 3,995,934 | 12/1976 | Nath .................. 350/96.32 |
| 4,009,382 | 2/1977 | Nath . |
| 4,045,119 | 8/1977 | Eastgate ............. 350/96.32 |
| 4,685,766 | 8/1987 | Nishimura et al. .......... 350/96.32 |
| 4,747,662 | 5/1988 | Fitz ..................... 350/96.32 |
| 4,927,231 | 5/1990 | Levatter ............. 350/96.32 |

FOREIGN PATENT DOCUMENTS

| | | |
|---|---|---|
| 0349126 | 1/1990 | European Pat. Off. . |
| 0375354 | 3/1990 | European Pat. Off. . |
| 0375178 | 6/1990 | European Pat. Off. . |
| 0381461 | 8/1990 | European Pat. Off. . |
| 2406424 | 5/1983 | Fed. Rep. of Germany . |
| 54-25745 | 2/1979 | Japan ............... 350/96.32 |
| 57-30802 | 2/1982 | Japan ............... 350/96.32 |
| 57-30804 | 2/1982 | Japan ............... 350/96.32 |
| 1274128 | 5/1972 | United Kingdom ........ 350/96.32 |
| 1502445 | 2/1975 | United Kingdom . |

OTHER PUBLICATIONS

Brochure entitled Teflon Amorphous Fluoropolymer distributed by DuPont.

*Primary Examiner*—Richard R. Cole
*Attorney, Agent, or Firm*—Handal & Morofsky

[57] ABSTRACT

A flexible light guide consists essentially of a flexible tube made of an amorphous fluoropolymer based on a combination of terafluoroethylene and a fluorinated cyclical ether, and a transparent liquid filling the tube. The liquid has an index of refraction which is higher than that of the material of the tube. The light guide may be provided with means for continously passing the liquid through the tube. In this case, the liquid may be physiological sodium chloride solution and the light guide may be a part of an endoscopic illumination device useful for endoscopic coagulation.

8 Claims, 1 Drawing Sheet

FLEXIBLE LIGHT GUIDE HAVING A LIQUID CORE AND ILLUMINATING DEVICE INCLUDING A LIGHT GUIDE OF THIS TYPE

FIELD OF THE INVENTION

The present invention relates to flexible light guides comprising a flexible tube of a transparent fluoropolymer containing a transparent liquid core having a higher refractive index than that of the thermoplastic resin. The invention relates further to illuminating devices comprising a flexible light guide of this type.

DESCRIPTION OF THE RELATED ART

A flexible light guide consisting essentially of a tube of polyvinyl chloride or 4-methyl pentene-1 polymers, a plug of a transparent material at either end of the tube to close the tube, and a transparent fluid "core" within the tube filling it, wherein the fluid has a refractive index greater than that of the polymer and consists of nitrobenzene, camphor, linseed oil, chlorobenzene, caster oil or benzyl alcohol is described in U.S. Pat. No. 3,740,113 (Cass).

A flexible light guide consisting essentially of a flexible tube made of fluoropolymers, such as polytetrafluoroethylene, polytrifluorochloroethylene and the copolymers of tetrafluoroethylene and hexafluoropropylene, and containing an aqueous salt solution is disclosed in my U.S. Pat. No. 4,009,382.

U.S. Pat. No. 4,747,662 (Fitz) discloses a flexible light guide ("fiber optics") having a liquid core, which comprises a liquid of high radiation transmission, and a sheath or tube made from a fluorine-containing polymer material wherein the fluorine-containing polymer material is a copolymer which comprises at least 20% by weight and at most 75% by weight of copolymerized units of vinylidene fluoride and copolymerized units of at least one further fluorine-containing monomer.

SUMMARY OF THE INVENTION

I have discovered that an improved such light guide may be provided by manufacturing the flexible tube of an amorphous fluorocarbon resin (fluoropolymer) which is based on a combination of tetrafluoroethylene and a fluorinated cyclical ether.

A suitable fluoropolymer of this type is TEFLON ® AF manufactured by Du Pont. This material has the following formula:

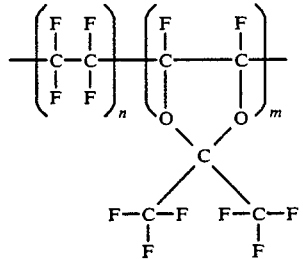

The ether acts as spacer for the main chain of the polymer and impedes sterically the crystallisation.

This fluoropolymer is clear as glass and has an exceptionally low index of refraction from 1.315 down to 1.29 (with increasing glass-point temperature (Tg)). There is thus made possible to use filling liquids which are more stable against the effects of short-wave ultraviolett radiation; the transmission is increased because the clear, truly amorphous material of the tube exhibits less absorption and scattering of the radiation at total reflection.

In preferred embodiments, the liquid core of the light guide is comprised of an aqueous fluoride. In another preferred embodiment, the light guide is open at both ends and is provided with means for passing liquid, such as physiological salt (NaCl) solution continuously through the tube.

DESCRIPTION OF THE PREFERRED EMBODIMENTS

Figure 1:
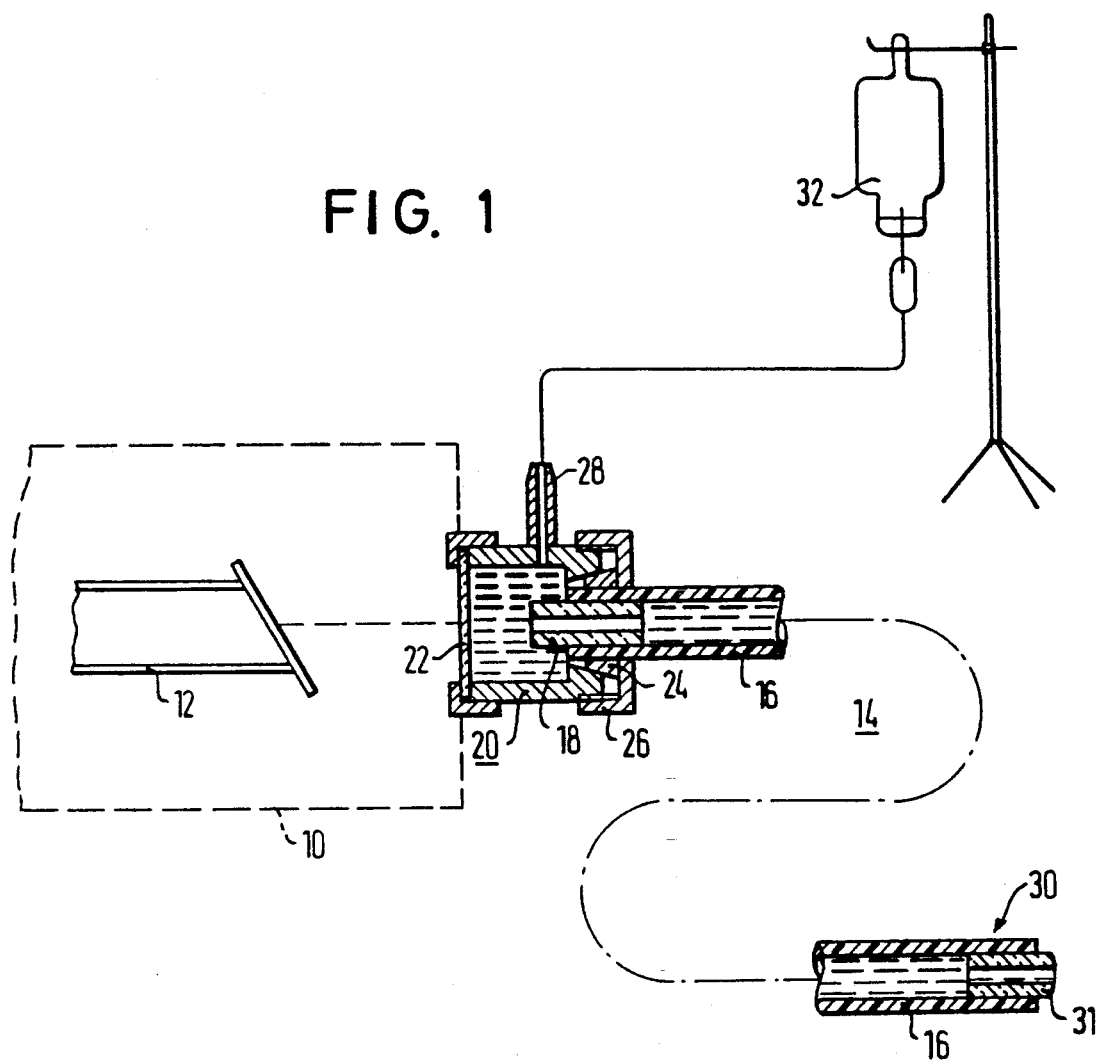
FIG. 1 is a schematical view, not to scale, of a first embodiment of the invention.

There is shown in FIG. 1 a schematical view partially in section of an illuminating device according to the invention. The illuminating device comprises a light source 10 which includes a XeCl excimer laser and a flexible light guide 14. The light guide 14 comprises a tube 16 made of an amorphous fluoropolymer which has the formula:

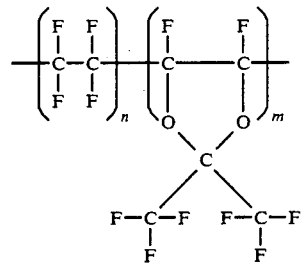

and is based on a combination of tetrafluoroethylene and a fluorinated cyclical ether.

A suitable fluoropolymer is Teflon ® AF 2400 (Du Pont) which has an index of refraction $n=1.29$.

Since this fluoropolymer is relatively stiff, the inner diameter of the tube generally will not exceed 3 mm and the wall thickness will generally not exceed 0.3 mm.

Suitable dimensions are:
Inner diameter 2 mm; wall thickness 0.25 mm.
Inner diameter 1 mm; wall thickness 0.15 mm.

A tubular plug having an axial bore and being made of ultraviolet transmissive quartz glass is positioned in a first end of the tube 16 which is adjacent to the light source 10. This end is mounted in an aperture of a rear wall of a tubular housing 20 and sealed with respect to aperture by a conical sealing ring 24 fixed by a screw cap 26. The front wall of the housing 20 is formed by a quartz window 22. The housing is further provided with a short pipe 28 through which a light transmissive liquid is introduced into the housing and, thus, through the axial bore of the plug 18 into the flexible tube 16. A plug 31 made of fused quartz and having an axial bore is force-fitted into a second, distal end 30 of the flexible tube 16.

The illuminating device described with reference to FIG. 1 is useful for endoscopic purposes it is exceptionally well suited for illuminating and coagulation within the body of a human being or an animal, e.g. within blood vessels. In applications of this type, the pipe 28 is connected to a sterile bag 32 containing physiological salt solution (normal saline; 0.9% NaCl) which is caused to flow slowly through the tube 16 and out of the open end 30. Contamination of the light exit end of the light guide by coagulated tissue, blood and the like is thus avoided. Since the filling liquid is continuously replaced, no problems in respect to long-term stability exist as they are encountered with the known flexible light guides having a filling liquid which contains an aqueous chloride solution.

Other types of lasers, e.g. argon and other excimer lasers and other types of light sources, such as incandescent lamps or gas discharge lamps may be used instead of the mentioned laser.

The plug 31 at the distal end of the light guide may be omitted. The window 22 may be formed by a lens which focusses the radiation of the light source into the light entrance end of the light guide.

Figure 2:
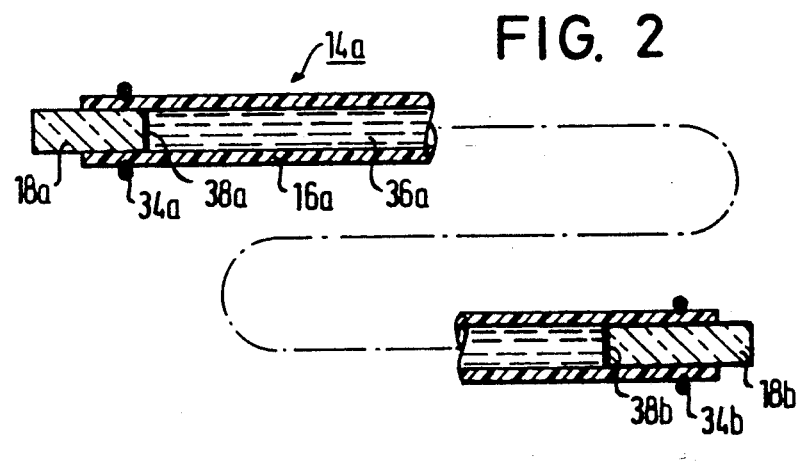
FIG. 2 is a schematical section of a flexible light guide according to a second embodiment of the invention.

FIG. 2 shows a flexible light guide 14a according to another embodiment of the invention. The light guide 14a has a tube 16a made of the amorphous fluoropolymer mentioned in connection with FIG. 1. The tube is closed at both ends by plugs 18a, 18b made of ultraviolet transmissive fused quartz and additionally sealed by O-rings 34a, 34b. The tube 16a is filled with a light transmissive liquid 36a, which is comprised of an aqueous solution of a fluoride and has an index of refraction which is higher than that of the material of the tube 16a. The liquid 36a may comprise at least one of the fluorides KF, NaF, NH4F, CsF. A low concentration of the fluoride is sufficient because of the low index of refraction of the material of the tube 16a. The plugs 18a, 18b are provided at the inner front surface and on the circumferential surface with a protective coating 38a, 38b, respectively, of the above-mentioned fluoropolymer to protect the plugs against the corrosive effects of the fluoride solution and any hydrofluoric acid formed by decomposition of the fluoride.

Fluorides are much more stable against intense ultraviolet radiation and have a higher transmissivity for ultraviolet radiation than chlorides.

The light guide of FIG. 2 is preferably used in an illuminating device which comprises a light source, such as a gas discharge lamp, as a mercury high pressure lamp, a xenon high pressure lamp, a tungsten-halogene lamp, or a laser such as an argon or excimer laser. The light exit surface of the plug 18b may be provided with an anti-sticking coating (not shown).

Other liquids may be used as filling liquid or core 36a of the light guide 14a of FIG. 2, e.g. water, preferably extremely pure water (aqua purissima). With an index of refraction of 1.29 of the tube material, a solid angle of the numerical aperture of the light guide of 37° can be obtained; with physiological salt solution even 42°. This is acceptable for light sources comprising an UV laser or a gas discharge lamp.

The outer surface of the fluoropolymer tube 16a of the sealed light guide of FIG. 2 may be coated with a thin layer of metal applied e.g. by vapor deposition to prevent the liquid 36a from diffusing out of the tube 16a. Alternatively, the tube 16a may be surrounded by a mantle tube which has a somewhat greater inner diameter than the outer diameter of the tube 16a to form a space which is filled with the same liquid as used within the tube 16a or with the solvent component of this liquid.

Other filling liquids may be used as the case may be, those liquids including fully-halogenated, more specifically fully-fluorinated aliphatic compounds as Fluorinert (Tradename 3M), aqueous solutions of fluorides, chlorides and phosphates, alcohols, glycols, including monoethyleneglycol, diethyleneglycol and triethyleneglycol, silicon oil, such as phenylmethysiloxane.

The windows and plugs may be made of sapphire. This material is resistant against fluorides, thus no protective coating is needed.

The term "light" as used herein is intended to include visible, infrared and ultraviolet radiation.

The "infusion" device described with reference to FIG. 1 may be filled initially with a physiologically compatible X-ray contrast medium to assist positioning of the front end of the light guide e.g. in an obstructed blood vessel, and the contrast medium may than be displaced by physiological salt solution to secure effective light transmission for perforating the obstruction.

The tube 16 of the device of FIG. 1 may be made of another fluorine containing polymer which has an index of refraction about 3/100 less than that of physiological salt solution at the wavelength used, such as 308 nm. For visible light the index of refraction of physiological salt solution is 1.34, thus the index of refraction of the tube material should be no more than about 1.31.

I claim:

1. A flexible light guide for illuminating a cavity comprising a flexible tube of a transparent fluorocarbon resin, said tube having a first end, a second end and an axial opening in said second end, said guide further comprising a transparent liquid within the tube filling it, said liquid having an index of refraction which is higher than that of said fluorocarbon resin, wherein said fluorocarbon resin is an amorphous fluoropolymer comprising a combination of tetrafluoroethylene and a fluorinated cyclic ether and liquid supply means for supplying said liquid into said tube at said one end thereof, whereby said liquid can flow through said tube while keeping it filled and emerge endwise from said axial opening into said cavity.

2. The flexible light guide as claimed in claim 1 wherein said amorphous fluoropolymer has the chemical formula

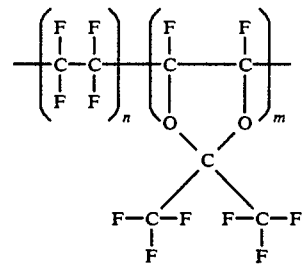

3. The flexible light guide as claimed in claim 1 wherein a light source is optically coupled to a first end of said tube.

4. The flexible light guide as claimed in claim 1 wherein said liquid supply means comprises a source of infusible physiological salt solution.

5. The flexible light guide as claimed in claim 1, wherein said first end is optically coupled to a light source comprising an excimer laser.

6. An illuminating device comprising a light source, and a flexible light guide as claimed in claim 1, said light source being optically coupled to an end of said light guide.

7. A flexible light guide according to claim 1 wherein said liquid supply means constitutes gravity feed means and said flexible tube further comprises a plug in said second end of said tube said plug having a restricted lengthwise bore for egress of said gravity-fed liquid in a continuous manner while keeping said flexible tube filled.

8. A flexible light guide according to claim 7 adapted for endoscopic use wherein said liquid is physiological saline solution.

* * * * *